United States Patent [19]
Wollweber et al.

[11] 3,970,699
[45] July 20, 1976

[54] 4-ACYLAMINOPHENYLACETAMIDINES AND A METHOD FOR THEIR PREPARATION

[75] Inventors: Hartmund Wollweber; Ekkehard Niemers; Hans Peter Schulz; Herbert Thomas; Peter Andrews, all of Wuppertal, Germany

[73] Assignee: Bayer Aktiengesellschaft, Germany

[22] Filed: Sept. 13, 1974

[21] Appl. No.: 505,738

[30] Foreign Application Priority Data
Sept. 18, 1973  Germany............................ 2346939

[52] U.S. Cl............................. 260/562 R; 424/324
[51] Int. Cl.²...................................... C07C 103/34
[58] Field of Search ................................ 260/562 R

[56] References Cited
UNITED STATES PATENTS
3,818,070   6/1974   Wollweber et al.............. 260/302 R Primary Examiner—C. Davis

[57] ABSTRACT

New 4-acylaminophenylacetamidines of the formula:

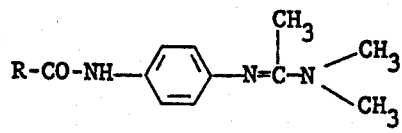

in which R is a straight or branched chain alkoxyalkyl having 3 to 8 carbon atoms or straight or branched chain alkenyloxyalkyl having 3 to 8 carbon atoms wherein the alkoxy moiety or alkenyloxy moiety may substituted by alkoxy or phenyl, and including the non-toxic pharmacologically acceptable salts thereof. The products have utility as parasiticides.

The products are obtained by either of two methods: (1) via the reaction of an N'-(4-aminophenyl)-N,N-dimethylacetamidine with an acylating agent or (2) via the reaction of a 4-acylaminoaniline with an N,N-dimethylacetamide or N,N-dimethylthioacetamide.

27 Claims, No Drawings

4-ACYLAMINOPHENYLACETAMIDINES AND A METHOD FOR THEIR PREPARATION

This invention relates to new 4-phenyl-acetamidines and to a method for their preparation. The products have utility as parasiticides.

It is stated in German Published Specification No. 2,029,299 that N'-phenyl-N,N-dimethylacetamidines are active against helminths. However these compounds exhibit a relatively low therapeutic index.

This invention describes novel products which also exhibit anthelmintic activity, particularly parasiticidal activity and which possess an improved therapeutic index.

The novel products of this invention are 4-acylaminophenylacetamidines of the following formula:

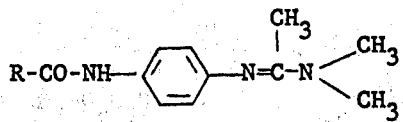

wherein
R is straight or branched chain alkoxyalkyl having 3 to 8 carbon atoms unsubstituted or substituted by 1 or 2 of the same or different members selected from the group consisting of alkoxy and phenyl; or straight or branched chain alkenyloxyalkyl having 3 to 8 carbon atoms unsubstituted or substituted by 1 or 2 of the same or different members selected from the group consisting of alkoxy and phenyl;
and the non-toxic pharmacologically acceptable salts thereof. These products combine a strong parasiticidal effect with a very good therapeutic index.

One embodiment of this invention comprises the following 4-acylaminophenylacetamidines:

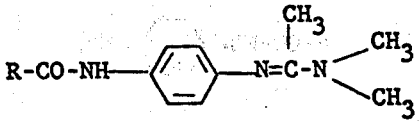

wherein
R is straight or branched chain alkoxyalkyl having 3 to 8 carbon atoms, either unsubstituted or substituted in the alkoxy moiety by one or two of the same or different members selected from the group consisting of alkoxy of 1 to 4 carbon atoms and phenyl; or straight or branched chain alkenyloxyalkyl having 3 to 8 carbon atoms, either unsubstituted or substituted in the alkoxy moiety by one or two of the same or different members selected from the group consisting of alkoxy of 1 to 4 carbon atoms and phenyl;
and the non-toxic pharmacologically acceptable salts thereof.

A second embodiment of this invention relates to those 4-acylaminophenylacetamidines of the following formula:

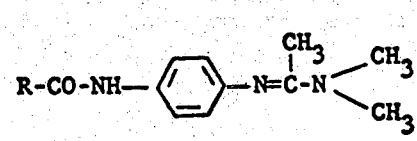

wherein
R is straight or branched chain alkoxyalkyl having 3 to 8 carbon atoms, either unsubstituted or substituted in the alkoxy moiety by one or two of the same or different members selected from the group consisting of alkoxy of 1 or 2 carbon atoms and phenyl; or straight or branched chain alkenyloxyalkyl having 3 to 8 carbon atoms, either unsubstituted or substituted in the alkoxy moiety by one or two of the same or different members selected from the group consisting of alkoxy of 1 or 2 carbon atoms and phenyl;
and the non-toxic pharmacologically acceptable salts thereof.

A preferred embodiment of this invention relates to 4-acylaminophenylacetamidines of the following formula:

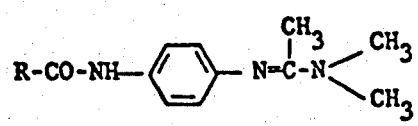

wherein
R is ethoxymethyl, propoxymethyl, butoxymethyl, isobutoxymethyl, isopropoxymethyl, t.-butoxymethyl, amyloxymethyl, isoamyloxymethyl, α-methoxypropyl, β-methoxypropyl, α-ethoxypropyl, β-ethoxypropyl, α-propoxypropyl, β-propoxypropyl, α-isopropoxypropyl, β-isopropoxypropyl, α-methoxybutyl, β-methoxybutyl, γ-methoxybutyl, α-ethoxybutyl, β-ethoxybutyl, γ-ethoxybutyl, allyloxymethyl, crotyloxymethyl, α-allyloxypropyl, β-allyloxypropyl, α-crotyloxypropyl, β-crotyloxypropyl, benzyloxymethyl, α-benzyloxypropyl, β-benzyloxypropyl, methoxyethoxymethyl or ethoxyethoxymethyl;
and the non-toxic pharmacologically acceptable salts thereof.

The following products are illustrative of the 4-acylaminophenylacetamidines of this invention:

N'-(ethoxyacetylaminophenyl)-N,N-dimethylacetamidine and its hydrochloride,
N'-(propyloxyacetylaminophenyl)-N,N-dimethylacetamidine and its hydrochloride,
N'-(i-propyloxyacetylaminophenyl)-N,N-dimethylacetamidine and its hydrochloride,
N'-(butyloxyacetylaminophenyl)-N,N-dimethylacetamidine and its hydrochloride,
N'-(i-butyloxyacetylaminophenyl)-N,N-dimethylacetamidine and its hydrochloride,
N'-(methoxymethylacetylaminophenyl)-N,N-dimethylacetamidine and its hydrochloride,
N'-(methoxypropionylaminophenyl)-N,N-dimethylacetamidine and its hydrochloride,
N'-(ethoxypropionylaminophenyl)-N,N-dimethylacetamidine and its hydrochloride,
N'-(α-methylpropyloxyacetylaminophenyl)-N,N-dimethylacetamidine and its hydrochloride,
N'-(γ,γ-dimethylpropyloxyacetylaminophenyl)-N,N-dimethylacetamidine and its hydrochloride,
N'-(allyloxyacetylaminophenyl)-N,N-dimethylacetamidine and
N'-(crotyloxyacetylaminophenyl)-N,N-dimethylacetamidine.

The 4-acylaminophenylacetamidines of this invention are substantially less toxic and approximately as active against hookworm of dogs, *Ancylostoma caninum* when compared against the known product N'-(4-aminophenyl)-N,N-dimethylacetamidine. Thus, for example, when compared against the known product N'-(methoxyacetylaminophenyl)-N,N-dimethylacetamidine, the products of this invention exhibit a substantially better parasiticidal effect and a more advantageous therapeutic index. This improvement in the therapeutic index for the instant products is of particular advantage in the treatment of helminthiases in animals.

The products (I) of this invention are obtained by either of two methods.

a. One such method consists of treating an aminophenylacetamidine of the formula:

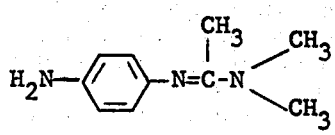  (II)

with the acylating agent:

R—CO—Z   (III)

wherein
Z is a carbonyl-activating radical which can be easily split off; and
R is as defined above.

Illustrative of the carbonyl-activating radicals within the definition of Z are, for example, halo, preferably chloro and bromo, anhydride, hydroxy, or alkoxy, alkenyloxy and aryloxy which may optionally be substituted in conducting this process. When the aminophenylacetamidine reactant (II) is treated with the acylating agent an acid binding reagent is generally used when Z in the acylating agent represents hydroxy; alternatively, when the acylating agent is other than hydroxy, a condensation agent, that is, a dehydrating agent, is generally employed. Illustrative of suitable acid binding agents are, for example, organic and inorganic bases such as sodium and potassium hydroxides, sodium bicarbonate, potassium carbonate, triethylamine and pyridine. Preferred condensation agents which may be employed in this process include, for example, inorganic acid halides such as phosphorus oxychloride, or phosphorous trichloride, thionyl chloride, phosgene, boron, trifluoride, a dialkyl sulphate such as dimethyl sulphate or diethyl sulphate, and organic acid halides such as benzoyl chloride and p-toluenesulphonic acid chloride. The following equation illustrates this method of preparation; however, it is to be understood that the ethoxyacetylchloride and N'-(4-aminophenyl)-N,N-dimethylacetamide which are used as starting materials in the following equation are illustrative only and, in practice, any aminophenylacetamidine and acylating agent falling within the scope of formulae II and III, supra, can be substituted therefor in an otherwise similar process to afford the instant products (I):

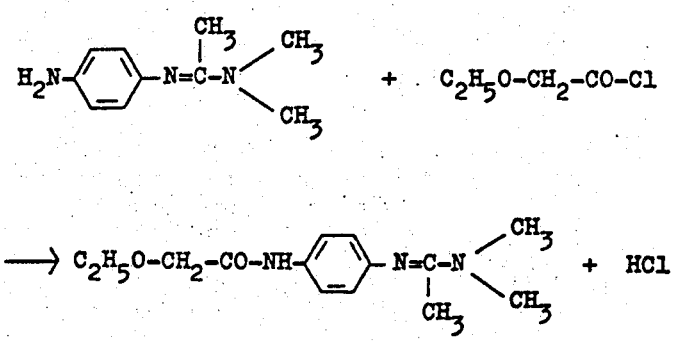

b. A second method for preparing the instant products (I) consists in treating an acylaminoaniline of the formula:

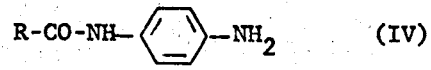   (IV)

wherein R is as defined above, with N,N-dimethylacetamide, N,N-dimethylthioacetamide or a functional derivative of N,N-dimethylacetamide. This process is preferably conducted in the presence of a condensation agent. Preferred condensation agents include, for example, inorganic acid halides such as phosphorus oxychloride, phosphorus trichloride, thionyl chloride, phosgene, boron, trifluoride, a dialkyl sulphate such as dimethyl sulphate or diethyl sulphate, and organic acid halides such as benzoyl chloride and p-toluenesulphonic acid chloride. Also, when N,N-dimethylthioacetamide itself is employed, mercury containing condensation agents such as mercuric oxide are preferably used. The following equation illustrates this method of preparation; however, it is to be understood that the 4-ethoxyacetylaminoaniline and N,N-dimethylacetamide which are employed as starting materials in the following equation are merely illustrative of the reactants which may be utilized and, in practice, any reactants falling within the scope of formula (IV), supra, is to be considered as being within the scope of this invention:

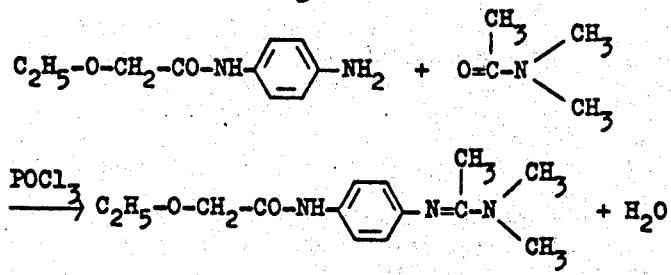

As indicated above, various functional derivatives of the N,N-dimethylacetamide depicted in the foregoing equation may be utilized in this process. Typical of these functional derivatives are, in addition to N,N-dimethylthioacetamide, the following: N,N-dimethylthioacetamide, N,N-dimethylacetamide-dialkylacetals, N,N-dimethylthioacetamide-dialkylacetals, 1-dimethylamino-1-alkoxy-ethylene and 1-dimethylamino-1-alkylmercapto-ethylene.

Both of the foregoing methods for preparing the instant products employ similar reaction conditions. Both processes can be carried out in the presence of an inert diluent such as an aromatic hydrocarbon, as, for example, benzene, toluene or xylene, or, alternatively, chlorinated hydrocarbons may be used as, for example, chlorobenzene, dichlorobenzene and tetrachloroethylene.

The reaction temperatures in both processes can be varied over a wide range but, in general, the reaction is conducted at a temperature of between about 10° and 130°C, preferably, at between about 20° and 120°C.

The proportions in which the starting materials are combined is not particularly critical to either of the instant processes and, in general, the reactants are usually combined in approximately equimolar amounts. In addition, the acylating agents and dehydrating agents employed in these processes are also used in equimolar quantities.

In practice, both of the instant processes are effected by simply combining the reactants either in the presence or absence of a solvent. Thereafter, the reaction mixture is preferably heated as, for example, at temperatures of 80° to 120°C. The resulting products can then be isolated by pouring the reaction mixture into water, separating out the desired product, drying and then recrystallizing or distilling the final product.

The good anti-parasitic activity and low toxicity of the instant products (I) is believed to be attributed to their ability to maintain a relatively stable level in the blood, generally, at a concentration of between about 4 and 8 γ/ml.

In particular, the products of this invention exhibit a surprisingly good and broad range of effectiveness against the following helminths, that is, nematodes and cestodes:

I. Nematodes

1. *Ancylostoma caninum*, *Uncinaria stenocephala* and *Bunostomum trigonocephalum* (hookworms) from the family of the Ancylostomatidae;

2. *Haemonchus contortus*, *Trichostrongylus colubriformis*, *Cooperia punctata*, *Ostertagia circumcincta*, *Nippostrongylus muris* and *Nematospiroides dubius* (stomach worms and worms of the small intestine) from the family of the Trichostrongylidae;

3. *Oesophagostomum columbianum* and *Chabertia ovina* (worms of the large intestine) from the family of the Strongylidae;

4. *Strongyloides ratti* (dwarf threadworms) from the family of the Rhabditidae;

5. *Toxocara canis*, *Toxascaris leonina* and *Ascaris suum* larvae (maw worms) from the familae of the Ascaridae or Anisakidae;

6. *Aspiculuris tetraptera* (pin-worms) from the family of the Oxyuridae;

7. *Heterakis spumosa* from the family of the Heterakidae.

II. Cestodes

1. *Hymenolepis nana* and *Hymenolepis microstoma* (tapeworms) from the superfamily of the Taenioidea.

This activity is illustrated by the following results.

Hookworm Test in Dog

Dogs experimentally infected with *Ancylostoma caninum* were treated after the expiration of the prepatency period of the parasites.

The active compound (I) was administered orally in the amount indicated as pure active compound or as a 10% strength solution in lactic acid in gelatine capsules.

The degree of effectiveness was determined by counting the worms expelled after the treatment and the worms remaining in the test animal, after dissection, and calculating the percentage of the worms expelled.

Table 1 below compares the maximum dose in mg/kg survived by mice after peroral administration (column I) with the dose, in mg/kg, at which, after peroral administration, 90% of all worms have been expelled (column II).

Table 1

$$R-CO-HN-\underset{}{\bigcirc}-N=C(CH_3)-N(CH_3)_2$$

| R | I | II |
|---|---|---|
| H (Known Product) | 100 | 5 |
| $CH_3-O-CH_2$ (Known Product) | 500 | 25 |
| $C_2H_5-O-CH_2-$ | 250 | 5 |
| $C_3H_7O-CH_2-$ | 250 | 10 |
| Iso-$C_3H_7O-CH_2-$ | 1000 | 10 |
| $C_4H_9O-CH_2-$ | 100 | 5 |
| Iso-$C_4H_9O-CH_2-$ | 250 | 5 |
| $CH_3O-CH(CH_3)-$ | 1000 | 10 |
| $CH_3O-CH_2-CH_2$ | 500 | 5 |
| $C_2H_5-O-CH_2-CH_2$ | 500 | 5 |
| $C_2H_5-CH(CH_3)-O-CH_2-$ | 500 | 10 |
| $(CH_3)_2CH-CH_2-CH_2-O-CH_2-$ | 1000 | 5 |

From the foregoing data, it is apparent that the compounds of this invention are, in general, less toxic than closely related known products and, in addition, are approximately equally active against hookworm of dogs, *Ancylostoma caninum* but substantially more effective than the closely related R methoxymethyl compounds. The compounds of the present invention thus have a more desirable therapeutic index. The smaller concentration which need be employed for the instant products as compared to the known compounds offers particular advantages in the treatment of helminthiases since it is then possible to formulate a composition which is more easily administered.

The compounds (I) of this invention can be utilized as the active ingredient in anthelmintic compositions having utility in veterinary medicine. These compositions contain a major or minor amount of at least one compound (I) of this invention as, for example, from about 99.5 to 0.1%, preferably 95 to 0.5%, and most preferably from about 0.5 to 90% of the compound (I) in combination with a pharmaceutically acceptable non-toxic inert diluent or carrier. The diluent or carrier comprises one or more solid, semi-solid or liquid medium, filler or formulation adjuvant which is non-toxic, inert and pharmaceutically acceptable. Also, the instant compositions are preferably in dosage unit form; i.e., in physically discrete units containing a predetermined amount of the drug corresponding to a fraction or multiple of the dose which is calculated to produce the desired therapeutic response. The dosage units can contain one, two, three, four or more single doses or, alternatively, one-half, one-third or one-fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, it is generally advantageous to administer amounts of from about 0.1 to 50 mg of the compound (I) per kg of body weight per day. In some instances a sufficient therapeutic effect can be obtained at a lower dose while in others, a larger dose will be required. A preferred daily dosage is in the range of from about 50 mg to 5 g of the active ingredient (I).

Oral administration can be effected utilizing solid and liquid dosage unit forms such as powders, tablets, dragees, capsules, granulates, suspensions, solutions, ampoules or suppositories, and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

The diluents to be used in pharmaceutical compositions for formulation into tablets, dragees, capsules and pills include the following: (a) fillers and extenders: starch, sugars, mannitol, and silicic acid; (b) binding agents: carboxymethyl cellulose and other cellulose derivatives, alginates, gelatine and polyvinyl pyrrolidone; (c) moisturizing agents: glycerol; (d) disintegrating agents: agar-agar, calcium carbonate and sodium bicarbonate; (d) agents for retarding dissolution: paraffin; (f) resorption accelerators: quaternary ammonium compounds; (g) surface active agents: cetyl alcohol and glycerol monostearate; (h) adsorptive carriers: kaolin and bentonite; (i) lubricants: talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be constituted as a timed release or sustained release formulation so that they release only the active ingredient or, preferably, release the active ingredient in a particular part of the intestinal tract, possibly over a period of time. Thus, for example, the coatings, envelopes and protective matrices may be made, of polymeric substances or waxes.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carrriers as talc, bentonite, silicic acid, polyamide powder, animal and vegetable fats, waxes, paraffins, starch, tragacanth, cellulose derivatives, polyethylene glycols, silicones, talc and zinc oxide or mixtures of these substances. Liquid and semi-liquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present.

Formulations can also be administered as an aerosol, utilizing the usual propellants such as the chlorofluorohydrocarbons. The pharmaceutical compositions which are sprays can also contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The following examples are illustrative of the products (I) of this invention and the methods for their preparation.

EXAMPLE 1

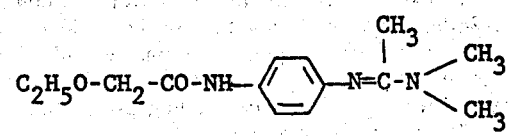

N'-(4-Aminophenyl)-N,N-dimethylacetamidine (212 g.) is dissolved in 500 ml of methylene chloride and added dropwise at 5°C to a solution of 161 g of ethoxyacetyl chloride in 500 ml of methylene chloride. The mixture is stirred for 30 minutes and evaporated in vacuo. The residue is then recrystallized from a mixture of ethyl acetate and alcohol and after filtration 326 g of N'-(ethoxyacetylaminophenyl)-N,N-dimethylacetamidine hydrochloride, melting point 186° – 187°C are obtained. The free base is obtained by addition of sodium hydroxide solution to afford the desired product having a boiling point of 192° – 194°C (0.1 mm Hg.).

By following the above procedure but substituting the appropriate acylating agent for the ethoxyacetyl chloride described therein, the following products are obtained.

Table 2

| R | Free Base: boiling point, °C | Hydrochloride melting point, °C | R—COCl |
|---|---|---|---|
| $C_3H_7$—O—$CH_2$— | 206–210/1 mm Hg. | 190–191 | propoxyacetyl chloride |
| $C_4H_9$—O—$CH_2$— |  | 194–196 | butoxyacetyl chloride |
| $(CH_3)_2CH$—O—$CH_2$— |  | 205–207 | isopropoxyacetyl chloride |
| $(CH_3)_2$—CH—$CH_2$—O—$CH_2$— | 196–200/0.1 mm Hg. | 202–204 | isobutoxyacetyl chloride |
| $CH_3$—$CH_2$—$CH(CH_3)$—O—$CH_2$— |  | 179–180 | sec.-butoxyacetyl chloride |
| $(CH_3)_2CH$—$CH_2$—$CH_2$—O—$CH_2$— |  | 193–195 | isoamyloxyacetyl chloride |
| $CH_3$—O—$CH(CH_3)$— |  | 202–204 | 2-methoxypropionyl chloride |
| $C_2H_5$—O—$CH(CH_3)$— |  | 183–185 | 2-ethoxypropionyl chloride |
| $CH_3$—O—$CH_2$—$CH_2$— |  | 199–201 | methoxypropionyl chloride |
| $C_2H_5$—O—$CH_2$—$CH_2$— |  | 167–169 | ethoxypropionyl chloride |
| $C_3H_7$—O—$CH_2$—$CH_2$— |  | 213–215 | propoxypropionyl chloride |
| $(CH_3)_2CH$—O—$CH_2$—$CH_2$— |  | 206–208 | isopropoxypropionyl chloride |
| $C_6H_5$—$CH_2O$—$CH_2$—$CH_2$— |  | 199–201 | benzyloxypropionyl chloride |
| $C_6H_5$—$CH_2$—O—$CH_2$— |  | 207–209 | benzyloxyacetyl chloride |
| $CH_2=CH$—$CH_2$—O—$CH_2$— | 196–198/0.1 mm Hg. | 197–199 | allyloxyacetyl chloride |
| $CH_2=C(CH_3)CH$—O—$CH_2$— | 194–196/0.1 mm Hg. |  | 2-isobutenyloxyacetyl chloride |
| $CH_3$—$CH=CH$—$CH_2$—O—$CH_2$— | 202–204/0.1 mm Hg. | 188–189 | 2-butenyloxyacetyl chloride |
| $CH_3O$—$CH_2$—$CH_2$—O—$CH_2$— |  | 183–185 | (2-methoxyethoxy)acetyl chloride |
| $CH_3$—O—$C(CH_3)_2$— |  | 152 | 2-methoxyisobutyryl chloride |

EXAMPLE 2

17.7 g of N'-(4-aminophenyl)-N,N-dimethylacetamidine in 50 ml of ethoxyacetic anhydride are heated to 100°C and evaporated in vacuo. The residue is rendered alkaline with sodium hydroxide solution and the organic phase is taken up in a mixture of chloroform/ether, and upon distillation in a vacuum, 22.5 g of N'-(4-ethoxyacetylaminophenyl)-N,N-dimethylacetamidine, boiling point (0.1 mm Hg. 192°–194°C is obtained.

EXAMPLE 3

79.5 g of phosphorus oxychloride is added dropwise at 20°C to 93.2 g of N,N-dimethylacetamide dissolved in 1,000 ml of toluene. The mixture is stirred for 3 hours at 20°C, whereafter 97 g of 4-ethoxyacetylaminoaniline is added and the resulting mixture is stirred overnight at 20°C and subsequently heated to 100°C for 1 hour. After decanting the toluene, the residue is taken up in a mixture of water and chloroform. Sodium hydroxide solution is then added with cooling and the organic phase is separated off. Upon distillation in vacuo 43 g of N'-(4-ethoxyacetylaminophenyl)-N,N-dimethylamidine, boiling point (0.1 mm Hg) 192° – 194°C, is obtained.

Upon substituting phosgene or para-toluenesulphonic acid chloride or dimethyl sulphate for the phosphorous oxychloride condensation agent, an identical product is obtained.

EXAMPLE 4

185 g of mercury oxide is added to a solution of 51.5 g of N,N-dimethylthioacetamide and 80 g of 4-ethoxyacetylaminoaniline in 500 ml of ethanol and the mixture is vigorously stirred for 8 hours at 0°C and then for 15 hours at 80°C. The precipitate is filtered off, the residue is distilled in vacuo and 18.6 g of N'-(ethoxyacetylaminophenyl)-N,N-dimethylacetamidine, boiling point (0.1 mm Hg) 192° – 194°C, is obtained.

EXAMPLE 5

19.4 g of 4-ethoxyacetylaminoaniline and 30 g of N,N-dimethylacetamide-diethylacetal are gradually heated to 80° – 100°C until the theoretical amount of alcohol has been split off. Upon distillation of the reaction product, 21 g of N'-(4-ethoxyacetylaminophenyl)-N,N-dimethylacetamidine, boiling point (0.1 mm Hg) 192° – 194°C, is obtained.

An identical product is obtained if, instead of N,N-dimethylacetamide-diethylacetal, the following reactants are used: 1-dimethylamino-1-ethoxyethylene, 1-dimethylamino-1-methoxyethylene, N,N-dimethylacetamide-dimethylacetal or N,N-dimethylthioacetamide-S,S-dimethylacetal.

What is claimed is:

1. A compound of the formula:

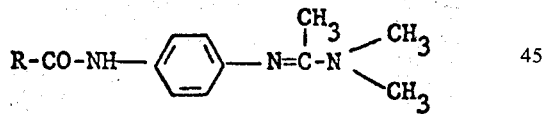

or a pharmaceutically acceptable non-toxic salt thereof wherein
R is straight or branched chain alkoxyalkyl having 3 to 8 carbon atoms, either unsubstituted or substituted in the alkoxy moiety by one or two of the same or different members selected from the group consisting of alkoxy of 1 to 4 carbon atoms and phenyl; or straight or branched chain alkenyloxyalkyl having 3 to 8 carbon atoms either unsubstituted or substituted in the alkoxy moiety by one or two of the same or different members selected from the group consisting of alkoxy of 1 to 4 carbon atoms and phenyl.

2. A compound according to claim 1

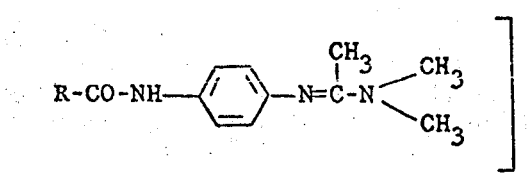

wherein
R is straight or branched chain alkoxyalkyl having 3 to 8 carbon atoms, either unsubstituted or substituted in the alkoxy moiety by one or two of the same or different members selected from the group consisting of alkoxy of 1 or 2 carbon atoms and phenyl; or straight or branched chain alkenyloxyalkyl having 3 to 8 carbon atoms, either unsubstituted or substituted in the alkoxy moiety by one or two of the same or different members selected from the group consisting of alkoxy of 1 or 2 carbon atoms and phenyl.

3. A compound according to claim 1

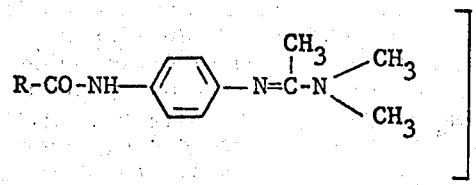

wherein
R is ethoxymethyl, propoxymethyl, butoxymethyl, isopropoxymethyl, isobutoxymethyl, sec.-butoxymethyl, isoamyloxymethyl, α-methoxyethyl, α-ethoxyethyl, methoxyethyl, ethoxyethyl, propoxyethyl, isopropoxyethyl, benzyloxyethyl, benzyloxymethyl, allyloxymethyl, 2-isobutenyloxymethyl, 2-butenyloxymethyl, (2-methoxyethoxy)methyl or α-methoxyisopropyl.

4. A compound according to claim 1

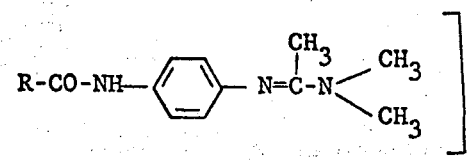

wherein
R is ethoxymethyl, propoxymethyl, butoxymethyl, isobutoxymethyl, isopropoxymethyl, t.-butoxymethyl, amyloxymethyl, isoamyloxymethyl, α-methoxypropyl, β-methoxypropyl, α-ethoxypropyl, β-ethoxypropyl, α-propoxypropyl, β-propoxypropyl, α-isopropoxypropyl, β-isopropoxypropyl, α-methoxybutyl, β-methoxybutyl, γ-methoxybutyl, α-ethoxybutyl, β-ethoxybutyl, γ-ethoxybutyl, allyloxymethyl, crotyloxymethyl, α-allyloxypropyl, β-allyloxypropyl, α-crotyloxypropyl, β-crotyloxypropyl, benzyloxymethyl, α-benzyloxypropyl, β-benzyloxypropyl, methoxyethoxymethyl or ethoxyethoxymethyl.

5. The compound according to claim 1 which is

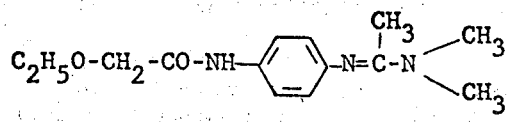

or the hydrochloride salt thereof.

6. The compound according to claim 1 which is

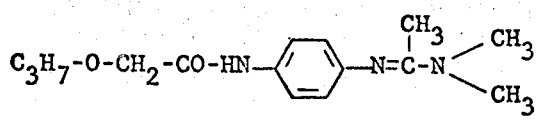

or the hydrochloride salt thereof.

7. The compound according to claim 1 which is

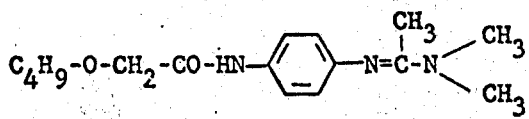

or the hydrochloride salt thereof.

8. The compound according to claim 1 which is

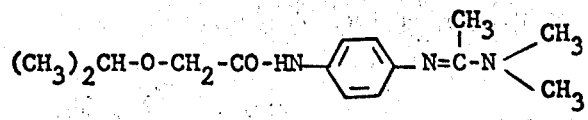

or the hydrochloride salt thereof.

9. The compound according to claim 1 which is

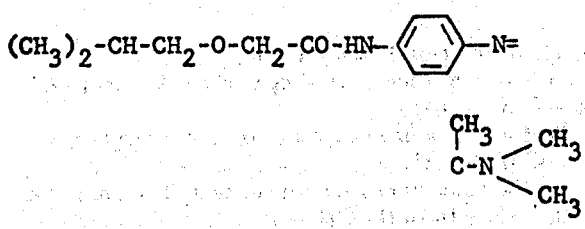

or the hydrochloride salt thereof.

10. The compound according to claim 1 which is

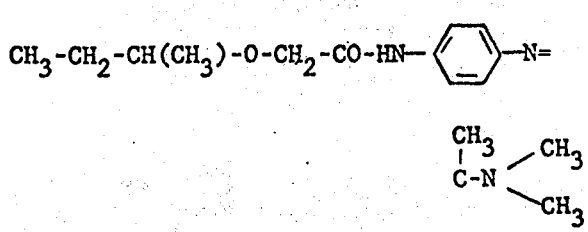

or the hydrochloride salt thereof.

11. The compound according to claim 1 which is

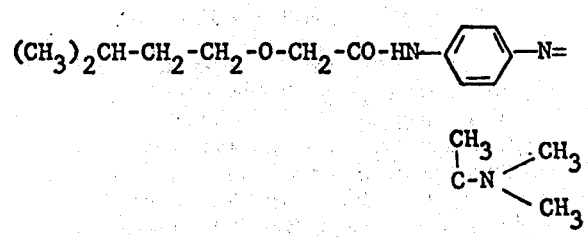

or the hydrochloride salt thereof.

12. The compound according to claim 1 which is

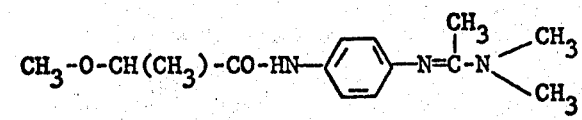

or the hydrochloride salt thereof.

13. The compound according to claim 1 which is

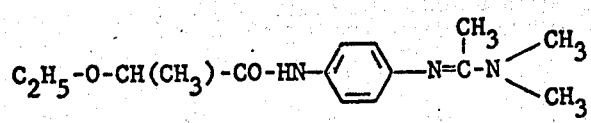

or the hydrochloride salt thereof.

14. The compound according to claim 1 which is

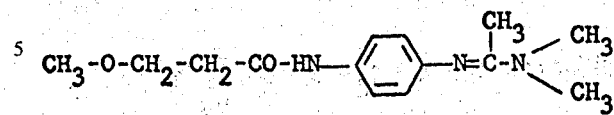

or the hydrochloride salt thereof.

15. The compound according to claim 1 which is

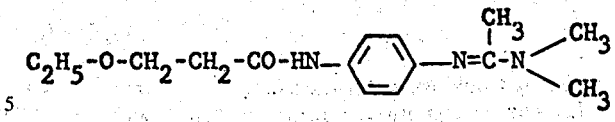

or the hydrochloride salt thereof.

16. The compound according to claim 1 which is

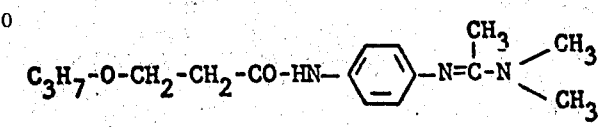

or the hydrochloride salt thereof.

17. The compound according to claim 1 which is

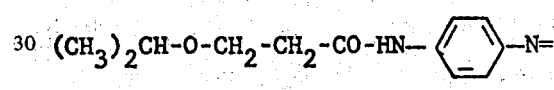

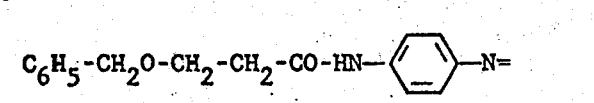

or the hydrochloride salt thereof.

18. The compound according to claim 1 which is

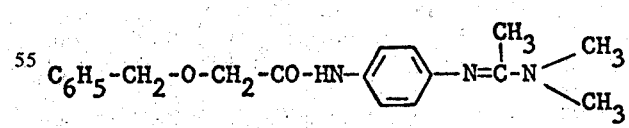

or the hydrochloride salt thereof.

19. The compound according to claim 1 which is

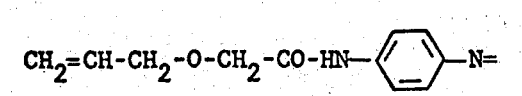

or the hydrochloride salt thereof.

20. The compound according to claim 1 which is

or the hydrochloride salt thereof.

21. The compound according to claim 1 which is

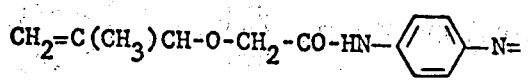
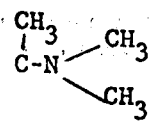

or the hydrochloride salt thereof.

22. The compound according to claim 1 which is

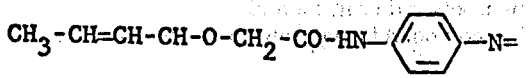
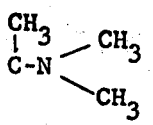

or the hydrochloride salt thereof.

23. The compound according to claim 1 which is

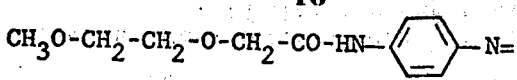
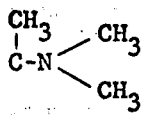

or the hydrochloride salt thereof.

24. The compound according to claim 1 which is

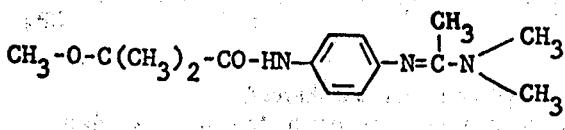

or the hydrochloride salt thereof.

25. The compound according to claim 1 wherein R is iso—$C_3H_7O$—$CH_2$—.

26. The compound according to claim 1 wherein R is iso—$C_4H_9O$—$CH_2$—.

27. The compound according to claim 1 wherein R is $C_2H_5$—$CH(CH_3)$—O—$CH_2$—.

* * * * *

UNITED STATES PATENT AND TRADEMARK OFFICE
CERTIFICATE OF CORRECTION

PATENT NO. : 3,970,699
DATED : July 20, 1976
INVENTOR(S) : Hartmund Wollweber; Ekkehard Niemers; Hans Peter Schulz; Herbert Thomas; Peter Andrews.

It is certified that error appears in the above-identified patent and that said Letters Patent are hereby corrected as shown below:

Please delete the structural formula in claims 2, 3 and 4 which is shown as follows:

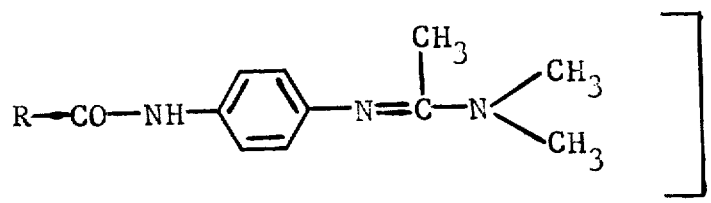

Signed and Sealed this

Nineteenth Day of October 1976

[SEAL]

Attest:

RUTH C. MASON
*Attesting Officer*

C. MARSHALL DANN
*Commissioner of Patents and Trademarks*